United States Patent
Aldridge

[19]

[11] Patent Number: 6,139,106
[45] Date of Patent: Oct. 31, 2000

[54] HEADREST FOR DENTAL USE

[76] Inventor: Kathleen M. Aldridge, 302 S. Arrawana, Tampa, Fla. 33609

[21] Appl. No.: 09/487,468

[22] Filed: Jan. 19, 2000

[51] Int. Cl.[7] .................................................... A47C 1/10
[52] U.S. Cl. ......................... 297/406; 297/407; 297/391
[58] Field of Search ................................... 297/408, 409, 297/406, 407, 391, 396, 397

[56] References Cited

U.S. PATENT DOCUMENTS

| | | |
|---|---|---|
| 638,534 | 12/1899 | Welch ..................................... 297/406 |
| 1,548,348 | 8/1925 | Case . |
| 3,216,767 | 11/1965 | Lutfy . |
| 3,719,388 | 3/1973 | Fortnam . |
| 3,885,831 | 5/1975 | Rasmussen . |
| 5,332,287 | 7/1994 | Whitmyer . |
| 5,586,810 | 12/1996 | Liu ......................................... 297/406 |

FOREIGN PATENT DOCUMENTS

| | | | |
|---|---|---|---|
| 142822 | 5/1985 | European Pat. Off. ................ | 297/406 |
| 148727 | 5/1985 | Japan ..................................... | 297/406 |

*Primary Examiner*—Laurie K. Cranmer
*Attorney, Agent, or Firm*—Matthew J. Peirce, Esq

[57] ABSTRACT

The present device is a small "U"-shaped, vinyl covered, foam filled pillow having two side mounted, hinged internal support arms which would adjust left and right with the use of a lock/unlock button. A follower arm is attached between the two support arms causing them to move left and right together, with the result that both would be positioned at the same angle when adjusted. When a patient's head is cradled in the pillow, a dentist or hygienist simply depresses the lock/unlock button, positions the head as desired, and releases the button to lock the arms in that position. Each side of the present invention has a foam head support pad that serves to secure the head and also provides comfort. An internal spring returns the support arms to the center or neutral position when the present invention is not in use. In order to allow the internal spring to return the support arms to the center or neutral position, the dentist or hygienist would depress the lock/unlock button.

1 Claim, 3 Drawing Sheets

HEADREST FOR DENTAL USE

BACKGROUND OF THE INVENTION

The present invention relates to a headrest for use in a dentist's office.

DESCRIPTION OF THE PRIOR ART

A wide variety of prior art discusses chairs and headrests for use by patients in dentist's offices. One example is U.S. Pat. No. 5,332,287, issued to Whitmyer, which discloses an articulating headrest of a type suitable for use in combination with a seating device.

U.S. Pat. No. 3,885,831, issued to Rasmussen, discloses an articulating headrest for treatment chairs such as dental chairs, to adapt such chairs for use in procedures with the dentist seated.

U.S. Pat. No. 3,719,388, issued to Fortnam, discloses a headrest assembly that has a head receiving depression in the front surface thereof for holding the head in a comfortable, yet secure position at all times.

U.S. Pat. No. 3,216,767, issued to Lutfy, discloses a chest rest assembly for use in combination with a chair, and in particular, to an improved dental chair characterized by means for supporting the chest of a dentist as he works upon a patient in a variety of positions.

U.S. Pat. No. 1,548,348, issued to Case, discloses a headrest for dental chairs and the like, comprising a bracket having diverging arms with rest pads mounted on the ends thereof.

U.S. Pat. No. 866,753, issued to Weber, discloses a headrest for use on a surgical, dental, or other chair, and pertains particularly to headrests wherein the rest proper is divided into two separate lateral sections or halves, each one of which is independently adjustable.

SUMMARY OF THE INVENTION

The present invention is a small "U"-shaped, vinyl-covered, foam-filled pillow having two side-mounted, hinged internal support arms which would adjust left and right with the use of a lock/unlock button. A follower arm is attached between the two support arms-causing them to move left and right together, with the result that both would be positioned at the same angle when adjusted. When a patient's head is cradled in the pillow, a dentist or hygienist would simply depress the lock/unlock button, position the patient's head as desired, and release the button to lock the arms in that position. Each side of the present invention has a foam head support pad that serves to secure the head and also provides comfort. An internal spring returns the support arms to the center or "neutral" position when the present invention is not in use. In order to allow the internal spring to return the support arms to the center or neutral position, the dentist or hygienist would depress the lock/unlock button.

The present invention can be incorporated into an existing dentist's chair. Alternatively, the present invention can be designed to be manufactured at the same time as a dentist's chair, allowing for easier incorporation of the present invention.

It is therefore an object of the present invention to provide a new and improved piece of medical equipment for a dentist's office.

It is therefore another object of the present invention to provide a new and improved piece of medical equipment that assists in cradling a patient's head and holding it to a desired angle while a dentist or hygienist works in the patient's mouth.

It is therefore another object of the present invention to provide a new and improved piece of medical equipment that provides comfort for a patient.

It is therefore another object of the present invention to provide a new and improved piece of medical equipment that provides ease of use for a dentist or hygienist.

It is therefore another object of the present invention to provide a new and improved piece of medical equipment that is easy to manufacture.

It is therefore another object of the present invention to provide a new and improved piece of medical equipment for a dentist's office that can either be incorporated into existing equipment or can be incorporated into a dentist's chair at the same time of manufacture.

Other objects, features and advantages of the present invention will become more readily apparent from the following detailed description of the preferred embodiment when considered with the attached drawings and appended claims.

DESCRIPTION OF THE PREFERRED EMBODIMENT

Figure 1:
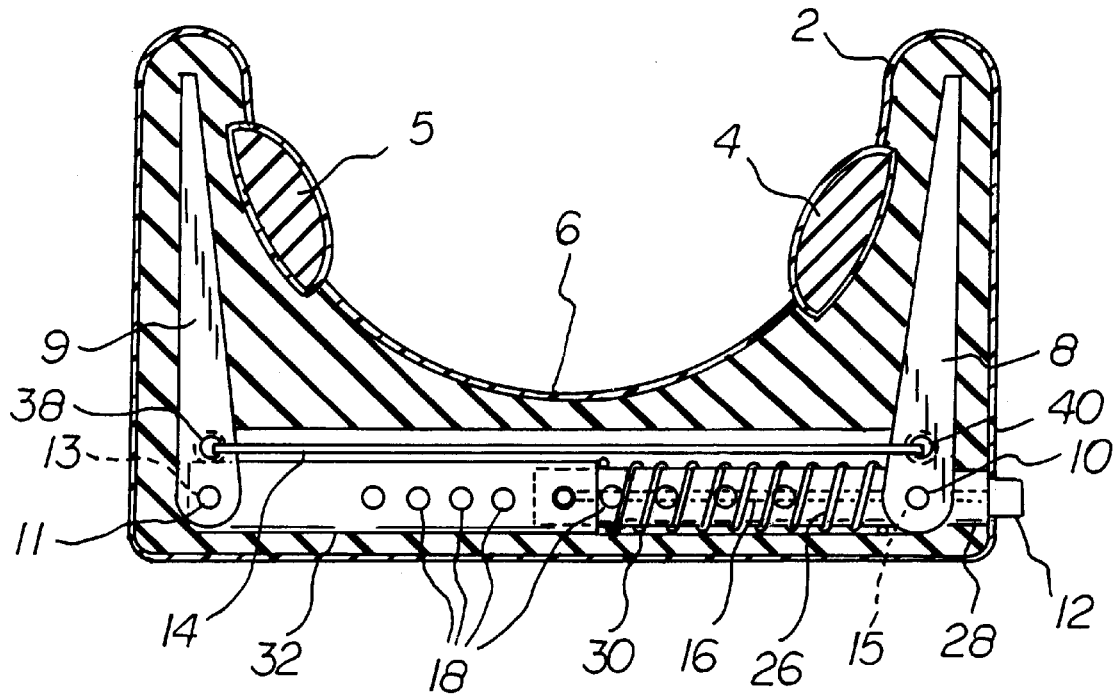
FIG. 1 shows a side cut away view of the present invention, covered by the vinyl covering.

FIG. 1 shows a side cut away view of the present invention, which is covered by a vinyl covering 2. The skeleton of the present invention is in a "U" shape, causing vinyl covering 2 to form a semicircular edge on the inside of the "U" of the skeleton of the present invention. The semicircular edge has head support pads 4 and 5, which are located opposite one another. The semicircular edge is designed to receive the back of a dental patient's neck in neck support 6, which is the lowest possible point of the semicircular edge of the present invention, with head support pads 4 and 5 providing support to the sides of the dental patient's head.

The skeleton of the present invention is comprised of outer support tube 32 and inner support tube 30, with inner support tube 30 telescoping wit outer support tube 32. Outer support tube 32 and inner support tube 30 each have a connected end and an extended end. The connected end of inner support tube 30 is connected to the connected end of outer support tube 32. Left support arm 9 is pivotly connected to the extended end of outer support tube 32 by hinges 11 and 13, while right support arm 8 is pivotly connected to the extended end of inner support tube 30 by hinges 10 and 15. Inner support tube 30 and outer support tube 32 each have a front face and a rear face.

Right support arm 8 and left support arm 9 are designed in the shapes of fulcrums, with both right support arm 8 and left support arm 9 including an inner side, an outer side, and two end sides, a front end side and a rear end side. The front end side and rear end side of both right support arm 8 and left support arm 9 extend further than the inner side and the outer side of both right support arm 8 and left support arm 9. The terminal ends of the front end side of left support arm 9 and the rear end side of left support arm 9 are pivotly connected to the extended end of outer support tube 32, while the front end side of right support arm 8 and the rear end side of right support arm 8 are pivotly connected to the extended end of inner support tube 30. The terminal end of the front end side of left support arm 9 is pivotly connected by hinge 11 to the front face of outer support tube 32. The terminal end of the rear end side of left support arm 9 is pivotly connected by hinge 13 to the rear face of outer support tube 32. The terminal end of the front end side of right support arm 8 is pivotly connected by hinge 10 to the front face of inner support tube 30. The terminal end of the rear end side of right support arm 8 is pivotly connected by hinge 15 to the rear face of inner support tube 30.

Linkage 16 is located within outer support tube 32 and inner support tube 30. Linkage 16 is a cylindrical metal rod that extends from approximately the extended end of outer support tube 32 to the extended end of inner support tube 30. At the extended end of inner support tube 30, linkage 16 culminates in push rod 28, which is a flat cylindrical plate located within inner support tube 30. Push rod 28 has an inner face and an outer face, with linkage 16 being connected to the inner face of push rod 28. Push rod 28 is rigidly connected to the inside of the extended end of inner support tube 30. Button 12 is attached to the outer face of push rod 28 and extends outside of the extended end of inner support tube 30.

Coiled spring 26 surrounds inner support tube 30 from the point of contact with outer support tube 32 to the extended end of inner support tube 30. Coiled spring 26 provides an outwardly extending tension upon outer support tube 32 and push rod 28, and returns right support arm 8 and left support arm 9 to a centered upright position when a dentist or other technician pushes button 12 and allows the tension in coiled spring 26 to be released.

The front faces of inner support tube 30 and outer support tube 32 include a plurality of adjustment holes 18 evenly spaced out in a linear row. The present invention also includes locking pin 20, which is fixedly attached to linkage 16 and is inserted through one of the adjustment holes 18 in order to fixedly lock inner support tube 30 and outer support tube 32 in a specific configuration.

The present invention also includes follower arm 14, which is a cylindrical metal rod with two ends, a first end and a second end. The first end of follower arm 14 is attached to the front end side of left support arm 9 by insertion through hole 38, which is a short distance above the location of hinge 11, while the second end of follower arm 14 is attached to the front end side of right support arm 8 by insertion through hole 40, which is a short distance above the location of hinge 10. Follower arm 14 serves to attach left support arm 9 to right support arm 8, and cause them to move left and right together, with the result that both right support arm 8 and left support arm 9 would be positioned at the same angle when the present invention would be adjusted.

The present invention is shown in a configuration that would be manufactured concurrently with a dentist's chair, and thus, would be incorporated into the dentist s chair. In an alternative embodiment, the present invention could be designed as an add-on to an existing dentist's chair. In this alternative embodiment, the present invention would also include some type of attachment means, such as Velcro or straps, which would allow the present invention to be firmly and securely placed on a standard dentist chair.

Figure 2:
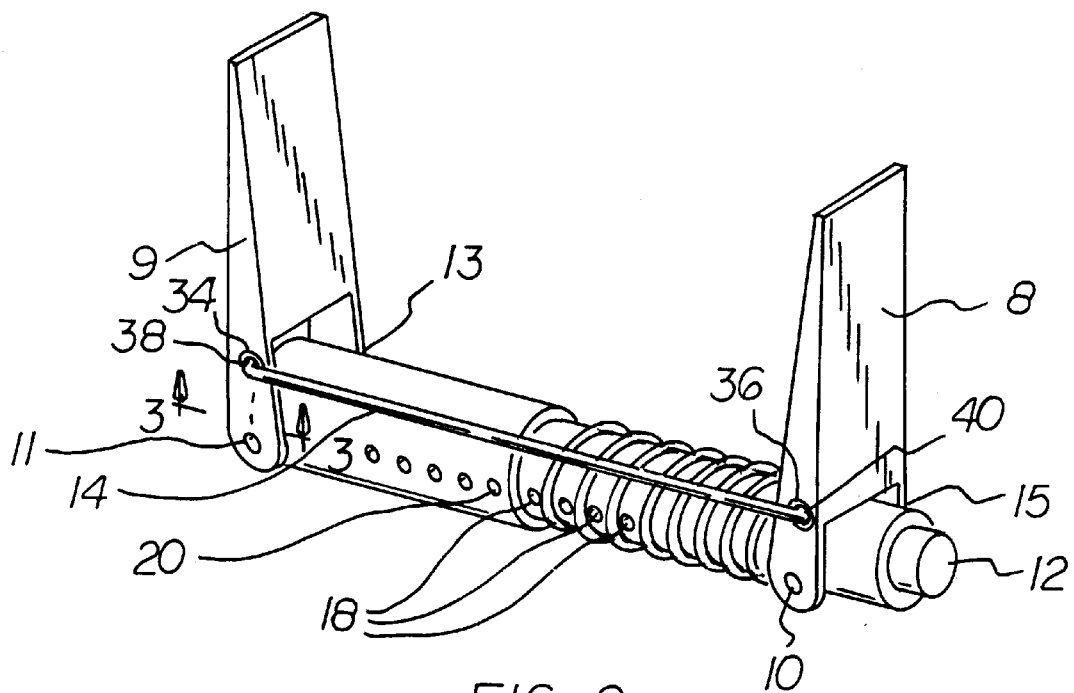
FIG. 2 is a perspective view of the present invention.

FIG. 2 is a perspective view of the present invention. Vinyl covering 2 has been removed so that the inner parts of the present invention may be seen.

Figure 3:
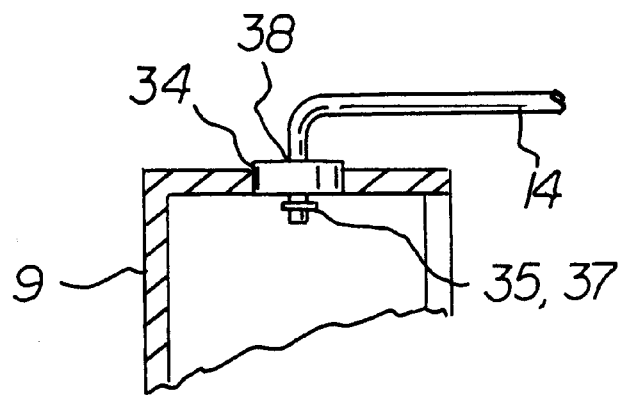
FIG. 3 is an end view of the connection of the first end of the follower arm with the left support arm.

FIG. 3 is an end view of the connection of the first end of follower arm 14 with left support arm 9. Follower arm 14 has an end-mounted hook which is inserted through hole 38. Hole 38 is located on bushing 34, which acts as a precision bearing. Bushing 34 can be made from nylon, plastic or bronze oilite material, either of which is durable and would provide long-lasting performance. The tip of follower arm 14 would include an end-mounted "E" clip 35 to prevent follower arm 14 from being pulled back out of hole 38.

The second end of follower arm 14 acts with right support arm 8 and hole 40 in an analogous manner along with bushing 36 and "E" clip 37.

Figure 4:
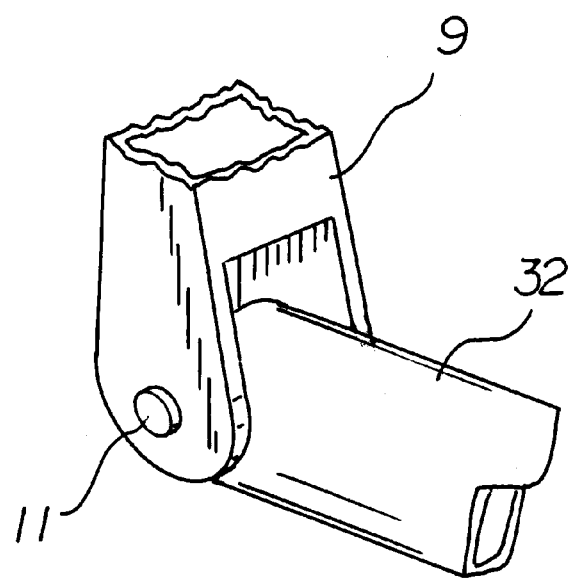
FIG. 4 shows a perspective view of the left support arm and the outer support tube as they are properly connected.

FIG. 4 shows a perspective view of left support arm 9 and outer support tube 32 as they are properly connected, along with the proper location of hinge 11 as it relates to left support arm 9 and outer support tube 32.

Figure 5:
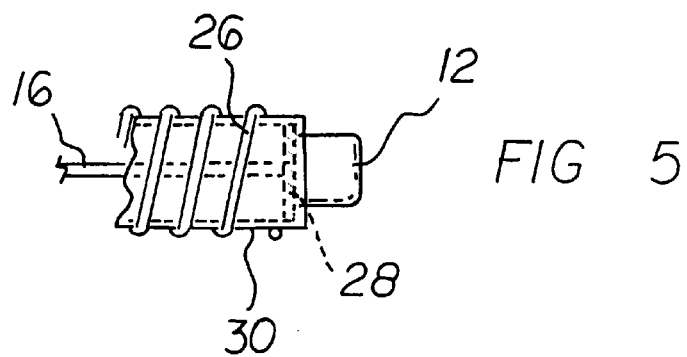
FIG. 5 shows a side view of the lock/unlock button as it is associated with the inner support tube.

FIG. 5 shows a side view of button 12 as it is associated with inner support tube 30. Push rod 28 is rigidly attached to button 12, while push rod 28 itself is rigidly fixed in place to a particular spot within the inside of inner support tube 30. Linkage 16 is fixedly attached to the center point on push rod 28. Coiled spring 26 surrounds the outside of inner support tube 30. When a user pushes button 12 in, button 12 itself does not push in but causes inner support tube 30 to be further telescoped within and pushed into outer support tube 32, thereby causing follower arm 14 to force the angle of right support 8 and left support arm 9 to be slightly adjusted. Locking pin 20 will also be forced in and could possibly be set in a different adjustment hole 18 once a user adjusts linkage 16 with button 12. In addition, this adjustment causes coiled spring 26 to have greater tension, thereby ensuring that the present invention will be forced back into a default position once button 12 is once again depressed.

Figure 6:
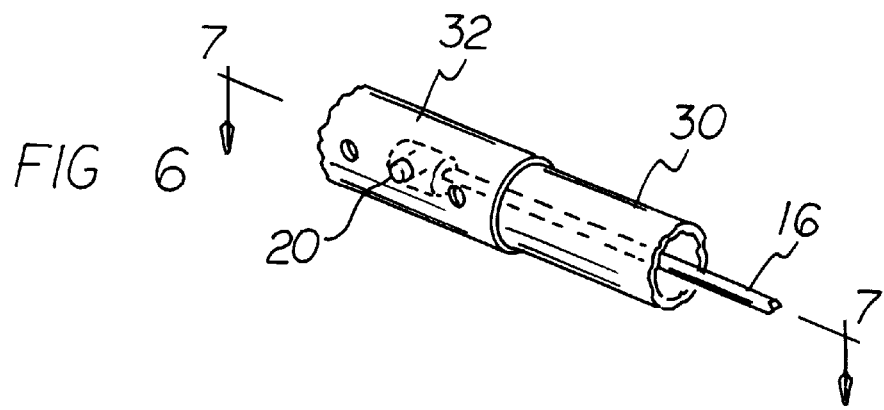
FIG. 6 shows a perspective view of the mechanisms surrounding the locking pin.
Figure 7:
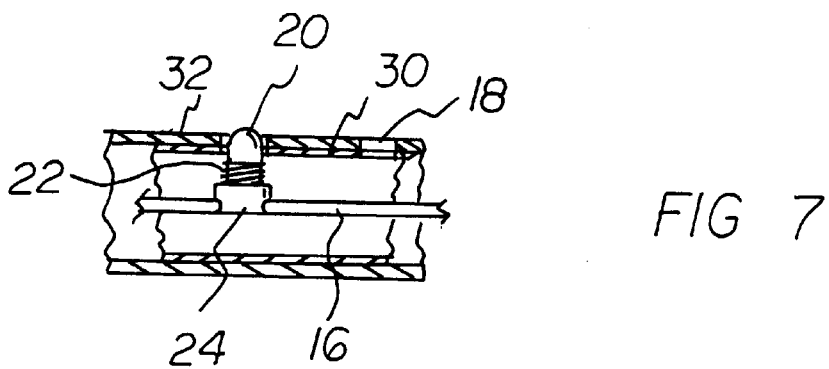
FIG. 7 shows a side view of the mechanisms surrounding the locking pin.

FIGS. 6 and 7 show perspective and side views, respectively, of the mechanisms surrounding locking pin 20. Locking pin 20 is attached to cam 24, which is attached to linkage 16. Locking pin 20 is constantly being pushed upward by spring 22, which circumferentially surrounds locking pin 20. Locking pin 20 has a top surface which is rounded, which allows locking pin 20 to easily be set within a particular adjustment hole 18 but also allows locking pin 20 to be gently forced out of a particular adjustment hole 18 by the horizontal movement, either by pushing or pulling, of linkage 16. In addition, linkage 16 can be rotated in such a manner that locking pin 20 will not be in alignment with the plurality of adjustment holes 18, thereby allowing a dentist or hygienist, when pushing button 12, to allow the present invention to return to its default position.

What I claim as my invention is:

1. A headrest for dental use, said headrest comprising:
    a. a base, said base comprising an outer support tube and an inner support tube, said inner support tube being telescoping within said outer support tube, said inner support tube having a front face and a rear face, said outer support tube having a front face and a rear face, said inner support tube including a plurality of holes placed in a linear row on the front face of said inner support tube, said outer support tube including a plurality of holes placed in a linear row on the front face of said outer support tube, said inner support tube including two ends, a connected end and an extended end, said outer support tube including two ends, a connected end and an extended end, said connected end of said inner support tube being in contact with said connected end of said outer support tube, b. a pair of support arms, a first support arm and a second support arm, both said first support arm and said second support arm designed in the shape of a fulcrum, both said first support arm and said second support arm including an inner side, an outer side, and two end sides, a front end side and a rear end side, said front end side and said rear end side of both said first support arm and said second support arm extending further down than said inner side and said outer side of both said first support arm and said second support arm, said first support arm and said second support arm each having a connected end and an open end, said connected end of said front end side of said first support arm pivotly mounted to the front side of said outer support tube, said connected end of said rear end side of said first support arm pivotly mounted to the rear face of said outer support tube, said connected end of said front end side of said second support arm pivotly mounted to the front face of said inner support tube, said connected end of said rear end side of said second support arm pivotly mounted to the rear face of said inner support tube, c. a linkage, said linkage being a cylindrical metal rod located within said outer support tube and said inner support tube, said linkage extending from approximately the extended end of said outer support tube to the extended end of said inner support tube, said linkeage including a locking pin, said locking pin extending outward from said linkage, said locking pin being circumferentially surrounded by a spring, said spring providing outwardly extending force upon said locking pin, d. a push rod, said push rod being a flat cylindrical plate rigidly fixated within said inner support tube near said extended end of said inner support tube, said push rod including an inner face and an outer face, said linkage being connected to the center point on the inner face of said push rod, e. a button, said button being attached to the outer face of said push rod, said button extending outside of the extended end of said inner support tube, f. a coiled spring, said coiled spring surrounding said inner support tube from the point of contact with said outer support tube to the extended end of said inner support tube, said coiled spring providing an outwardly extending tension upon said outer support tube and said push rod, g. a follower arm, said follower arm being a cylindrical metal rod with two ends, a first end and a second end, said first end of said follower arm being attached to said first support arm by insertion through a hole, said hole being located on said front side edge of said first support arm immediately above said pivotal attachment of said first support arm to said outer support tube, said second end of said follower arm being attached to a hole, said hole being located in the front side edge of said second support arm, said hole being located immediately above said pivotal attachment of said second support arm to said inner support tube, h. a vinyl covering, said vinyl covering enveloping the first support arm, said second support arm, said inner support tube, and said outer support tube, said vinyl covering forming a semicircular edge, said semicircular edge being used a head support, said semicircular edge including a pair of head support pads, a first head support pad and a second head support pad, said first head support pad being located opposite said second head support pad, said first head support pad and said second head support pad being designed to provide support to the sides of a dental patient's head, i. whereby a user pushes said button in, said button causes said push rod and said inner support tube to be further telescoped within said outer support tube, thereby causing said follower arm to adjust the angle of said first support and said second support arm, whereby said locking pin will be able to be set into one of said plurality of holes on said front face of said inner support tube and said outer support tube, whereby said coiled spring will be compressed and have greater tension.

\* \* \* \* \*